United States Patent
Nawaz et al.

(10) Patent No.: US 9,902,668 B2
(45) Date of Patent: Feb. 27, 2018

(54) HYDROGENATION REACTOR AND PROCESS

(71) Applicant: SAUDI BASIC INDUSTRIES CORPORATION, Riyadh (SA)

(72) Inventors: Zeeshan Nawaz, Riyadh (SA); Faisal Baksh, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/916,377

(22) PCT Filed: Aug. 29, 2014

(86) PCT No.: PCT/IB2014/002681
§ 371 (c)(1),
(2) Date: Mar. 3, 2016

(87) PCT Pub. No.: WO2015/033231
PCT Pub. Date: Mar. 12, 2015

(65) Prior Publication Data
US 2016/0214913 A1    Jul. 28, 2016

Related U.S. Application Data

(60) Provisional application No. 61/874,748, filed on Sep. 6, 2013.

(51) Int. Cl.
*B01J 8/00* (2006.01)
*B01J 8/02* (2006.01)
(Continued)

(52) U.S. Cl.
CPC ............... *C07C 5/333* (2013.01); *B01J 8/008* (2013.01); *B01J 8/0242* (2013.01); *B01J 8/0278* (2013.01);
(Continued)

(58) Field of Classification Search
CPC ....... B01J 8/00; B01J 8/008; B01J 8/02; B01J 8/0242; B01J 8/0278; B01J 8/0285;
(Continued)

(56) References Cited

U.S. PATENT DOCUMENTS 4,786,727 A * 11/1988 Schroeder .......... C07D 295/023
540/484
4,940,687 A    7/1990 Liu
(Continued)

FOREIGN PATENT DOCUMENTS

CN    202876771 U    4/2013
CN    204051634 U    12/2014
(Continued)

OTHER PUBLICATIONS

International Search Report and Written Opinion dated Jun. 9, 2015 by the International Searching Authority for application PCT/IB2014/002681, filed on Aug. 29, 2015 and published as WO 2015/033231 on Mar. 12, 2015 (Applicant—Saudi Basic Industries Corporation // Inventor—Nawaz, et al.) (15 pages).
(Continued)

*Primary Examiner* — Natasha Young
(74) *Attorney, Agent, or Firm* — Ballard Spahr LLP (57) ABSTRACT

A reactor and process for removing unsaturated alkynes and diolefinic impurities from olefins and oxygenates.

18 Claims, 3 Drawing Sheets

(51) Int. Cl.
| | |
|---|---|
| B01J 8/04 | (2006.01) |
| B01J 19/00 | (2006.01) |
| B01J 19/24 | (2006.01) |
| C07C 5/00 | (2006.01) |
| C07C 5/333 | (2006.01) |
| C10G 45/00 | (2006.01) |
| C10G 45/32 | (2006.01) |
| C10G 45/34 | (2006.01) |
| C10G 49/00 | (2006.01) |
| C07C 5/09 | (2006.01) |
| C07C 7/163 | (2006.01) |
| C07C 7/167 | (2006.01) |
| C07C 5/02 | (2006.01) |
| C07C 5/08 | (2006.01) |
| C07C 5/32 | (2006.01) |
| C07C 5/327 | (2006.01) |

(52) U.S. Cl.
CPC ........... *B01J 8/0285* (2013.01); *B01J 8/0492* (2013.01); *C07C 5/09* (2013.01); *C07C 5/3337* (2013.01); *C07C 7/163* (2013.01); *C07C 7/167* (2013.01); *C10G 45/34* (2013.01); *C10G 49/002* (2013.01); *B01J 2208/00017* (2013.01); *B01J 2208/00061* (2013.01); *B01J 2208/00132* (2013.01); *B01J 2208/00557* (2013.01); *B01J 2208/00893* (2013.01); *B01J 2208/00938* (2013.01); *B01J 2208/027* (2013.01); *B01J 2219/0004* (2013.01); *C07C 2523/44* (2013.01); *C10G 2300/1092* (2013.01); *C10G 2300/4018* (2013.01); *C10G 2300/70* (2013.01); *C10G 2400/20* (2013.01)

(58) Field of Classification Search
CPC ... B01J 8/04; B01J 8/0492; B01J 19/00; B01J 19/24; B01J 2208/00–2208/00044; B01J 2208/00061; B01J 2208/00106; B01J 2208/00115; B01J 2208/00132; B01J 2208/00548; B01J 2208/00557; B01J 2208/00798; B01J 2208/00893; B01J 2208/00938; B01J 2208/02; B01J 2208/021; B01J 2208/027; B01J 2219/00–2219/0004; C07C 5/00; C07C 5/02; C07C 5/08; C07C 5/09; C07C 5/32; C07C 5/327; C07C 5/333; C07C 5/3335; C07C 5/3337; C07C 7/00; C07C 7/148; C07C 7/163; C07C 7/167; C07C 2523/16; C07C 2523/40; C07C 2523/44; C10G 45/00; C10G 45/32; C10G 45/34; C10G 49/00; C10G 49/002; C10G 2300/00; C10G 2300/10; C10G 2300/1088; C10G 2300/1092; C10G 2300/40; C10G 2300/4018; C10G 2300/70; C10G 2400/00; C10G 2400/20

See application file for complete search history.

(56) References Cited

U.S. PATENT DOCUMENTS

| | | | |
|---|---|---|---|
| 5,190,731 A | 3/1993 | Stahl | |
| 5,898,091 A | 4/1999 | Chodorge | |
| 6,368,996 B1* | 4/2002 | Mu | B01J 25/02 |
| | | | 148/403 |
| 6,486,369 B1 | 11/2002 | Voight | |
| 6,717,025 B1 | 4/2004 | Risch | |
| 7,115,789 B2 | 10/2006 | Kuechler | |
| 7,301,062 B2 | 11/2007 | Gartside | |
| 2004/0122274 A1 | 6/2004 | Van Egmond | |
| 2004/0162357 A1 | 8/2004 | Eastland | |
| 2005/0037244 A1* | 2/2005 | Goetsch | B01J 12/007 |
| | | | 423/351 |
| 2006/0025641 A1 | 2/2006 | Gartside et al. | |
| 2007/0027030 A1* | 2/2007 | Cheung | B01J 23/44 |
| | | | 502/208 |
| 2010/0032347 A1 | 2/2010 | Ring et al. | |
| 2010/0312030 A1* | 12/2010 | Kibby | B01J 23/894 |
| | | | 585/310 |
| 2012/0305446 A1 | 12/2012 | Daily | |

FOREIGN PATENT DOCUMENTS

| | | |
|---|---|---|
| DE | 19804806 | 8/1999 |
| EP | 1350560 A1 | 10/2003 |
| EP | 1611945 A1 | 1/2006 |
| GB | 306442 | 7/1929 |
| GB | 865299 A | 4/1961 |
| GC | 32435 | 11/2016 |
| WO | WO-2015/033231 A2 | 3/2015 |

OTHER PUBLICATIONS

U.S. Appl. No. 61/874,748, filed Sep. 6, 2013, Nawaz (Saudi Basic Industries Corporation).
PCT/IB14/002681 (WO 2015/033231), Aug. 29, 2014, Nawaz (Saudi Basic Industries Corporation).
U.S. Appl. No. 62/259,756, filed Nov. 25, 2015, Nawaz.
PCT/IB2016/056962 (WO 2017/089936), Nov. 18, 2016 (Jun. 1, 2017), Nawaz (Saudi Basic Industries Corporation).

* cited by examiner

HYDROGENATION REACTOR AND PROCESS

CROSS-REFERENCE TO RELATED APPLICATIONS

The present application is a U.S. National Phase Application of International Application No. PCT/IB2014/002681, filed Aug. 29, 2014, now WO 2015/033231, which claims priority to U.S. Application No. 61/874,748, filed Sep. 6, 2013, all of which applications are incorporated herein fully by this reference.

BACKGROUND

Technical Field

The present disclosure relates to a hydrogenation reactor and process for removing unsaturated impurities from olefins and oxygenates.

Technical Background

The selective hydrogenation of alkynes is an integral process in the purification of olefin and oxygenate streams. Acetylenic and diolefinic impurities are inevitably present in such streams and should be removed or reduced to prevent catalyst poisoning and to meet target specifications for the downstream production of fine chemicals and polymers. For example, ethylene streams can typically comprise from about 0.1 to 3 mole % of acetylene, and propylene streams can typically comprise from about 0.5 to 10 mole % of propyne and/or propadiene. Ideally, the concentration of these acetylenic impurities should be reduced to levels of about 0.5 mole % or less and propyne and/or propadiene level should be less than 2.8 mole %.

Conventional processes for the hydrogenation of acetylene utilize a catalyst, such as a Pd-based catalyst that is modified with promoters. The generally accepted mechanism for acetylene hydrogenation is that acetylene adsorbs on the palladium metal sites on the catalyst, and then reacts with hydrogen. The availability of active palladium sites for the adsorption of acetylene impacts the selectivity of the catalyst. While hydrogenation of ethylene to ethane intrinsically occurs at a faster rate, the selective adsorption of acetylene on palladium can result in efficient acetylene hydrogenation if a sufficient quantity of acetylene exists to adsorb to active palladium metal sites.

Low concentrations of carbon monoxide can also be utilized as a reaction modifier in front-end acetylene converters. Carbon monoxide adsorbs to palladium more strongly than acetylene or conjugated diolefins, so it can prevent the adsorption of ethylene at even low concentrations.

Disadvantages of such hydrogenation/dehydrogenation processes include the production of alkanes, oligomers, and the formation of coke. In conventional high space velocity and low contact reactions (e.g., hydrogenation and dehydrogenation), uniform feed distribution and low pressure drops are desirable. Runaway reactions and hotspots that can affect production rates and selectivity are also common.

Accordingly, there is an ongoing need for new, efficient reactors and processes for hydrogenation and dehydrogenation reactions, such as for example, in processes for removing unsaturated impurities from olefins and oxygenates. These needs and other needs are satisfied by the compositions and methods of the present disclosure.

SUMMARY

In accordance with the purpose(s) of the invention, as embodied and broadly described herein, this disclosure, in one aspect, relates to a hydrogenation reactor and process for removing unsaturated impurities from olefins and oxygenates.

In one aspect, the present disclosure provides an integrated reactor design for removing alkynes, dienes, and/or mixture thereof from an olefin and/or oxygenate stream.

In another aspect, the present disclosure provides an integrated reactor design for removing alkynes, dienes, and/or mixture thereof from an olefin and/or oxygenate stream, wherein hydrogenation occurs in the presence of a catalyst with minimum contact time.

In another aspect, the present disclosure provides a reactor design that can useful for high throughput, fast reactions, such as, the dehydrogenation of alkane to alkenes.

In one aspect, the present disclosure provides a reactor suitable for use in a hydrogenation and/or a dehydrogenation process, the reactor comprising: a catalyst bed, a plurality of inlets for conveying a feed material to the catalyst bed; and one or more outlets, wherein the catalyst bed comprises a catalyst having a surface area of from about 15 $m^2/g$ to about 650 $m^2/g$, and wherein the reactor can provide a space velocity of from about 500/h to about 50,000/h for hydrogenation reactions or from about 1/h to about 1,000/h for dehydrogenation reactions.

In another aspect, the present disclosure provides a method for a dehydrogenation process, the method comprising introducing a feed material to the reactor described above through the plurality of inlets, such that the feed material uniformly or substantially uniformly contacts a catalyst bed to produce a reaction product.

In another aspect, the present disclosure provides a method for a hydrogenation process, the method comprising introducing a feed material to the reactor of claim 1 through the plurality of inlets, such that the feed material uniformly or substantially uniformly contacts a catalyst bed to produce a reaction product.

BRIEF DESCRIPTION OF THE FIGURES

The accompanying figures, which are incorporated in and constitute a part of this specification, illustrate several aspects and together with the description serve to explain the principles of the invention.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "a ketone" includes mixtures of two or more ketones.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not. For example, the phrase "optionally substituted alkyl" means that the alkyl group can or can not be substituted and that the description includes both substituted and unsubstituted alkyl groups.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

References in the specification and concluding claims to parts by weight of a particular element or component in a composition or article denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

As used herein, the term "space velocity" is intended to refer to the quotient of the entering volumetric flow rate of reactants divided by the reactor volume or the catalyst bed volume, unless specifically stated to the contrary. In one aspect, the space velocity can indicate how many reactor volumes of feed material can be treated in a unit time.

The term "alkyl group" as used herein is a branched or unbranched saturated hydrocarbon group of, for example, 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "alkoxy" as used herein is an alkyl group bound through a single, terminal ether linkage; that is, an "alkoxy" group may be defined as OR where R is alkyl as defined above. A "lower alkoxy" group is an alkoxy group containing from one to six carbon atoms.

The term "alkenyl group" as used herein is a hydrocarbon group of from 2 to, for example, about 24 carbon atoms and structural formula containing at least one carbon-carbon double bond. Asymmetric structures such as (AB)C=C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to, for example, about 24 carbon atoms and a structural formula containing at least one carbon-carbon triple bond.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "carbonate group" as used herein is represented by the formula —OC(O)OR, where R can be hydrogen, an alkyl, alkenyl, alkynyl, aryl, aralkyl, cycloalkyl, halogenated alkyl, or heterocycloalkyl group described above.

The term "carboxylic acid" as used herein is represented by the formula —C(O)OH.

The term "aldehyde" as used herein is represented by the formula —C(O)H.

The term "keto group" as used herein is represented by the formula —C(O)R, where R is an alkyl, alkenyl, alkynyl, aryl, aralkyl, cycloalkyl, halogenated alkyl, or heterocycloalkyl group described above.

The term "carbonyl group" as used herein is represented by the formula C=O.

The term "ether" as used herein is represented by the formula AOA$^1$, where A and A$^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "sulfo-oxo group" as used herein is represented by the formulas —S(O)$_2$R, —OS(O)$_2$R, or, —OS(O)$_2$OR, where R can be hydrogen, an alkyl, alkenyl, alkynyl, aryl, aralkyl, cycloalkyl, halogenated alkyl, or heterocycloalkyl group described above.

Each of the materials disclosed herein are either commercially available and/or the methods for the production thereof are known to those of skill in the art.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

As briefly described above, the present disclosure provides processes and reactor designs for use in hydrogenation and/or dehydrogenation reactions. In one aspect, the reactor designs and/or processes can be useful for removing unsaturated impurities from olefins and/or oxygenate streams.

The selective hydrogenation of alkynes is an integral process in the purification of olefin and oxygenate streams. Acetylenic and diolefinic impurities are inevitably present in such streams and should be removed or reduced to prevent catalyst poisoning and to meet target specifications for the downstream production of fine chemicals and polymers. For example, ethylene streams can typically comprise from about 0.1 to 3 mol. % of acetylene, and propylene streams can typically comprise from about 0.5 to 10 mol. % of propyne and/or propadiene. Ideally, the concentration of acetylenic impurities should be reduced to levels of about 0.5 mole % or less and propyne and/or propadiene level should be less than 2.8 mole %.

Conventional processes for the hydrogenation of acetylene utilize a catalyst, such as a Pd-based catalyst that is modified with promoters. The generally accepted mechanism for acetylene hydrogenation is that acetylene adsorbs on the palladium metal sites on the catalyst, and then reacts with hydrogen. The availability of active palladium sites for the adsorption of acetylene impacts the selectivity of the catalyst. While hydrogenation of ethylene to ethane intrinsically occurs at a faster rate, the selective adsorption of acetylene on palladium can result in efficient acetylene hydrogenation if a sufficient quantity of acetylene exists to adsorb to active palladium metal sites.

Low concentrations of carbon monoxide can also be utilized as a reaction modifier in front-end acetylene converters. Carbon monoxide adsorbs to palladium more strongly than acetylene or conjugated diolefins, so it can prevent the adsorption of ethylene at even low concentrations.

Disadvantages of such hydrogenation/dehydrogenation processes include the production of alkanes, oligomers, and the formation of coke. In conventional high space velocity and low contact reactions (e.g., hydrogenation and dehydrogenation), uniform feed distribution and low pressure drops can be desirable. Runaway reactions and hotspots that can affect production rates and selectivity are also common.

In one aspect, the present disclosure provides a reactor and process for removing at least a portion of any unsaturated impurities that can be present in, for example, a gaseous mixture of olefins and/or oxygenate rich streams. In various aspects, the reactor design can be utilized as a front-end and/or a back-end acetylene removal unit (ARU). In another aspect, such a reactor can be used to remove acetylene from an olefin stream of, for example, ethylene.

In one aspect, the reactor of the present disclosure can comprise a commercially available catalyst, depending upon, for example, the specific impurities to be removed and the location of the unit. In one aspect, the reactor can utilize a supported catalyst. In another aspect, the reactor can utilize an unsupported catalyst. In another aspect, the reactor can be useful for both hydrogenation and dehydrogenation processes. In still another aspect, the reactor can be useful in high space velocity processes with low pressure drop. In yet another aspect, the reactor can provide flexibility beyond that attainable with conventional reactor designs, so as to avoid runaway reactions and/or hotspots. In contrast, conventional reactor designs can be subject to frequent runaway reactions In high space velocity processes, such as, for example, hydrogenation and dehydrogenation processes, the uniformity of a feed distribution can significantly affect the process. A uniform or substantially uniform feed can improve contact and turnover of the feed with the catalyst, and can, in various aspects, improve efficiency and selectivity of the process. Thus, in one aspect, the feed distribution is uniform or substantially uniform.

In one aspect, one or more of the reactors of the same or varying configuration can be used together. In one aspect, a single reactor can be used. In another aspect, two or more reactors can be used, for example, in a series or parallel arrangement.

In yet another aspect, the reactor can be used in an alkane dehydrogenation fixed bed process, for example, to convert alkanes to alkenes.

The reactor and processes described herein can facilitate one or more interactive reactions having high space velocity, low pressure drop, superior flow, robust control of runaway reactions, control of hotspot formation, or a combination thereof.

Conventional reactors for hydrogenation and/or dehydrogenation reactions, such as, for example, the hydrogenation of acetylene, can utilize a palladium based catalyst modified with one or more promoters, such as, for example, Ag, Ga, Ru, Ni, Pb, Sn, Bi, Sb, Au, Cu, or a combination thereof. While not wishing to be bound by theory, the generally accepted mechanism is that acetylene adsorbs onto palladium metal sites on the catalyst. The adsorbed acetylene can be activated by the catalyst and react with hydrogen. The selectivity of the reaction can, in one aspect, be controlled by the availability of active palladium metal sites. While the intrinsic rate of ethylene hydrogenation is greater than that for acetylene, acetylene is more strongly adsorbed on palladium, resulting in high selectivity towards acetylene hydrogenation if sufficient acetylene exists to contact the palladium metal sites in a catalyst bed.

In various aspects, the reactor of the present disclosure can be used in a front-end configuration, a backend configuration, or a combination thereof. In a front-end configuration, the hydrogenation reactor can be positioned in the compression train of cracked gas, prior to removal of hydrogen, methane, and carbon monoxide, and for example, after a $C_2$ splitter and before a demethanizer. The feed material for such a front-end configuration can comprise acetylenic and/or olefinic compounds, with large amounts of hydrogen (e.g., from about 12 mol. % to about 45 mol. %). Typical $H_2$/alkyne ratios for such a configuration can range from about 5 to about 50, with carbon monoxide concentrations ranging from about 50 ppm to about 5,000 ppm. Carbon monoxide forms from an inverse water-gas shift reaction in cracking furnaces, and as, such, the concentrations of carbon monoxide can vary. It should also be noted that the values recited herein for a feed material are only intended to be exemplary, and that the present invention is not intended to be limited to any particular component and/or concentrations values.

In a back-end configuration, the reactor can be positioned after, for example, hydrogen, methane, and/or carbon monoxide removal steps. As such, hydrogen, for example, from about 1 vol. % to about 4 vol. %, and carbon monoxide can be added to the reactor feed or injected separately into the reactor. In one aspect, both front-end and back-end reactors can be operated at room temperature conditions, for example, from about 20° C. to about 40° C. and at pressures ranging from about 15 bar to about 30 bar. The performance of any given reactor or reaction can be affected by the presence of impurities such as, for example, Hg, $O_2$, COS, $H_2S$, $NH_3$, $PH_3$, and other compounds. In addition, lower ratios of hydrogen to acetylene can provide higher ethylene selectivity, as there may be insufficient acetylene to contact all catalyst sites.

Reactor

The reactor and processes of the present disclosure can be used alone or in combination with other components, reactors, and/or processes. In various aspects, the reactor and/or any components thereof can comprise any materials suitable for use in hydrogenation and/or dehydrogenation reactions as described herein. In one aspect, the materials of construction of such a reactor are inert or substantially inert to any feed materials, reactants, catalysts, products, byproducts, or other chemical compounds that can contact the reactor during normal operation. In one aspect, all or a portion of a reactor can be internally lined, for example, with a brick and/or ceramic material. In another aspect, a reactor or portion thereof can be constructed of any materials suitable for use at the process conditions and with the reactants and products of a given reaction. In another aspect, a reactor or portion thereof can comprise a stainless steel, such as, for example, 304 stainless steel and/or 316 stainless steel.

In another aspect, the size of the reactor or any portion thereof can vary, depending upon the specific feed material, product, and scale of operation desired. One of skill in the art, in possession of this disclosure, could readily select an appropriately sized reactor or components for use in a given reaction or process.

In one aspect, the reactor can comprise an enclosed vessel with one or more inlets and one or more outlets. In another aspect, the reactor can comprise a catalyst bed disposed inside the vessel, configured such that feed materials are contacted with the catalyst bed and remaining feed material and/or reaction products flow through and/or past the catalyst bed.

The reactor can comprise a plurality of inlets, capable of delivering and/or distributing a feed material to the catalyst bed. In various aspects, the reactor comprises 2, 3, 4, or more inlets. In another aspect, each of inlets can be positioned so as to direct a feed material onto a first side of a catalyst or catalyst bed or a portion thereof. In one aspect, the reactor comprises 2 inlets. In another aspect, the reactor comprises 3 inlets. In yet another aspect, the reactor comprises 4 inlets. In one aspect, the flow of feed material can be divided between the plurality, for example, 2, 3, 4, or more, inlets to distribute the feed material across the first side of the catalyst or catalyst bed. In another aspect, all or a portion of the plurality of inlets can be positioned so as to divide the flow of feed material into a plurality of equal or approximately equal flows. In another aspect, the reactor comprises a plurality of inlets for an individual reactor or stage in a process.

Any one or more of the plurality of inlets, if present, can optionally comprise one or more distributors for dispersing the feed material. A distributor can comprise any means for distributing and/or dispersing the feed material within the reaction vessel. In various aspects, the distributor can comprise a porous ceramic material, a sintered metal, a conduit with a plurality of openings, or a combination thereof. In other aspects, a distributor can comprise other materials and/or configurations not recited herein, but which can disperse a feed material. In one aspect, each of the plurality of inlets comprises a plurality of distributors. In another aspect, the use of a distributor can improve the flow of feed material to the catalyst and/or catalyst bed, such that the feed material more uniformly contacts the catalyst bed. In yet another aspect, the flow of feed material can be uniform or substantially uniform across the first side of the catalyst or catalyst bed. As used herein, the term substantially uniform is intended to describe an aspect wherein the flow of feed material is approximately equal across the first surface of the catalyst bed. In such an aspect, small variations in flow and/or concentration can still exist, but are significantly fewer and/or smaller than a comparable flow with a single inlet.

The reactor of the present disclosure can have a single or a plurality of outlets. In one aspect, the reactor can comprise a single outlet. In another aspect, the reactor can comprise a plurality, such as, for example, 2, 3, 4, or more, outlets. In one aspect, the reactor comprises a plurality of outlets and any two or more outlets can be combined downstream into a single flow. In another aspect, each of the outlets can be positioned so as to collect flow from a second side of the catalyst bed (i.e., a side opposing the first side). In such an aspect, unreacted feed material, reaction products, and/or byproducts flowing through and/or after having contacted the catalyst and/or catalyst bed, can be collected with the one or more outlets.

In one aspect, the reactor can further comprise one or more locations to collect condensate and/or oil, for example, green oil. Depending upon the geometric orientation of the reactor, the collection point (s) can be positioned so as to collect condensate and/or oil via gravity. Thus, in one aspect, a collection point can be provided at the bottom of a reactor vessel. In another aspect, the design of the reactor vessel can be such that any condensate and/or oil produced and/or recovered will flow to the one or more collection points. For example, the lower portion of a reactor can be bowl shaped so as to collect condensate and/or oil at a single point. In another aspect, a pan and/or drip tray can be utilized within the reactor to assist in the collection of condensate and/or oil.

The catalyst used in a particular reaction can be selected depending upon the specific reaction, feed material, impurities, and desired product. In various aspects, the catalyst can be disposed in a bed, such that the feed material contacts the catalyst bed. In one aspect, the catalyst bed is disposed between the plurality of inlets and the one or more outlets of the reactor. The catalyst bed can be of any thickness suitable for use with a particular reaction. In one aspect, the catalyst bed does not substantially impede the flow of feed material and/or reaction products through the reactor (i.e., from inlet to outlet). In another aspect, the catalyst bed can contact the interior walls of the reactor, separating the flow of feed material from the inlets and the flow of reaction products to the outlet(s). The reactor can be designed so that a first gas space exists between the inlets and the catalyst bed, and that a second gas space exists between the catalyst bed and the outlet(s). In one aspect, such a gas space, for example, between the inlets and the catalyst bed can facilitate distribution of the feed material across the catalyst bed.

The catalyst bed can be supported at one or more points within the reactor. In one aspect, a plurality of supports can be used to position the catalyst bed within the reactor and prevent movement. In a specific aspect, a reactor can be designed with inlets disposed on the top surface and outlet(s) disposed on the bottom surface. In such an aspect, the catalyst bed can be disposed horizontally within the reactor, supported by a plurality of supports between the bottom surface of the catalyst bed and the interior bottom wall of the reactor. It should be noted that this aspect is only intended to be exemplary, and that no specific geometric orientations are implied or deemed necessary for the present invention. The composition of the catalyst bed can comprise any suitable catalyst and/or support materials conventionally used in hydrogenation and/or dehydrogenation reactions, or that one of skill in the art would identify for use in such a reaction. Catalyst systems for hydrogenation and dehydrogenation reactions are known and commercially available.

During use and depending upon the specific reaction and catalyst used, the catalyst bed and/or reactor can exhibit a change in temperature. For exothermic reactions, the catalyst bed and/or reactor can exhibit significant increases in temperature. Similarly, for endothermic reactions, the catalyst bed and/or reactor can exhibit significant decreases in temperature. For some reactions and/or catalyst systems, it can be important to maintain reactor and/or catalyst bed temperature within a target range for improved efficiency or to prevent damage to the catalyst. Thus, in one aspect, the reactor can comprise one or more thermowells that can be used for measuring temperature inside the reactor or catalyst bed. In one aspect, such thermowells can be positioned to extend from an exterior surface of the reactor to a location within the catalyst bed. The ability to monitor temperature within the reactor can be useful in optimizing efficiency and preventing overheating or deterioration of the catalyst or reactor components.

In another aspect, a mechanism for heating and/or cooling the catalyst bed and/or reactor can be employed. In various aspects, such a mechanism can comprise heating elements or tubes for use in heating or cooling the catalyst bed. In another aspect, any suitable means for controlling and/or adjusting the temperature of the reactor or catalyst bed can be utilized. In one aspect, tubes can be disposed in the catalyst bed, wherein a fluid, for example, water, can flow to adjust the temperature of the catalyst bed. In one aspect, a single winding tube or a plurality of tubes can be disposed in a catalyst bed, wherein a fluid can flow through the tube to reduce the temperature of the catalyst bed. The fluid can optionally be refrigerated and/or recirculated as needed to maintain a desirable temperature in the catalyst bed.

In one aspect, the reactor can be utilized in a front-end configuration. In such an aspect, the reactor can be positioned in the compression train of cracked gas, prior to removal of hydrogen, methane, and carbon monoxide. In another aspect, the reactor can be positioned downstream from a $C_2$ splitter. In yet another aspect, the reactor can be positioned upstream of a demethanizer. When used in a front-end configuration, the feed material can comprise acetylenic and/or olefinic compounds. In one aspect, such a feed material can comprise a large amount of hydrogen (e.g., from about 12 mol. % to about 45 mol. %).

In another aspect, the reactor can be utilized in a back-end configuration. In such an aspect, the reactor can be positioned downstream of hydrogen, methane, and/or carbon monoxide removal units. In one aspect, the reactor can be positioned downstream of a hydrogen removal unit, such that hydrogen comprises from about 1 vol. % to about 4 vol. % of the reactor feed. In another aspect, the reactor can be positioned downstream of a carbon monoxide removal unit or elsewhere, such that no or minimal amounts of carbon monoxide are present in the feed. In such an aspect, carbon monoxide can be added to the reactor feed prior to the reactor or injected directly into the reactor.

In other aspects, the reactor can be operated in a continuous manner, wherein a steady flow of feed material is present. In another aspect, the reactor can be operated in a batch manner, wherein a given amount of feed material is injected through the plurality of inlets in a single pulse or over a fixed period of time, after which the flow of feed material is halted. In yet another aspect, the reactor can be operated in a semi-batch process, wherein a portion of the reactor is used in an operational mode while a separate portion of the reactor is operated in a regenerative mode. In such an aspect, one or multiple inlets can be in an operational mode, while another one or multiple inlets can be used for regeneration, either simultaneously or in, for example, alternating cycles. In such an aspect, the catalyst or a portion thereof can be regenerated as needed without completely stopping a process. In an optional aspect, one or more dividers or baffles can be used within the reactor to isolate portions thereof and allow for separate, simultaneous, operational and rengerative operations.

As previously noted, a plurality of individual reactors can be utilized in series and/or parallel configurations. In various aspects, 2, 3, 4, 5, 6, 7, 8, 9, 10, or more individual reactors can be used in a process. In an exemplary two-bed reactor system, two reactors are disposed in series in a front-end configuration. This exemplary system can be used for the hydrogenation of, for example, acetylene. For depropanizer applications, from about two to about four, for example, two, three, or four, individual reactors can be utilized. In one aspect, the concentration of undesirable components can necessitate a given number of reactors. In a similar aspect, when used for dehydrogenation reactions, from about one to, for example, about ten reactors can be utilized in a parallel manner.

In other aspects, the current invention is intended to encompass hydrogenation and/or dehydrogenation processes wherein a feed material is conveyed to a reactor, catalyst, and/or catalyst bed via a plurality of inlets, for example, 2, 3, 4, 5, 6, or more inlets. In another aspect, the current invention is intended to encompass hydrogenation and/or dehydrogenation processes wherein reaction products, byproducts, and/or unreacted feed material is conveyed from a reactor, catalyst, and/or catalyst bed via one, two, three, or more outlets.

In various aspects, the reactor can be utilized as a front and/or back-end acetylene removal unit with an ethylene or other olefin stream, for example, in a series or parallel configuration. In another aspect, the reactor can be utilized in an alkane dehydrogenation fixed bed process for conversion of alkanes to alkenes. In one aspect, the reactor design described herein can provide one or more of: high space velocity, low pressure drop, improved flow distribution, and/or improved control and/or prevention of runaway reactions. In other aspects, any two or more, three or more, or four of the benefits described herein can be attained by using the inventive reactor.

In one aspect, the reactor and/or a hydrogenation process can be operated at a space velocity of from about 500/h to about 50,000/h, for example, about 500, 1,000, 2,000, 3,000, 4,000, 5,000, 10,000, 15,000, 20,000, 25,000, 30,000, 35,000, 40,000, 45,000, or 50,000/h; from about 1,000/h to about 50,000/h; from about 10,000/h to about 50,000/h; from about 20,000/h to about 50,000/h; or from about 30,000/h to about 50,000/h, depending upon, for example, the particular catalyst used and the temperature of the reactor and/or catalyst bed.

In one aspect, the reactor and/or a hydrogenation process can be operated at a temperature of from about 20° C. to about 200° C., for example, about 20, 30, 40, 50, 60, 70, 80, 90, 100, 110, 120, 130, 140, 150, 160, 170, 180, 190, or 200° C.

In one aspect, the reactor and/or a dehydrogenation process can be operated at a space velocity of from about 1/h to about 1,000/h, for example, about 1, 2, 3, 4, 5, 8, 10, 15, 20, 25, 30, 35, 40, 45, 50, 55, 60, 65, 70, 75, 80, 90, 100, 150, 200, 250, 300, 350, 400, 450, 500, 550, 600, 650, 700, 750, 800, 850, 900, 950, or 1,000/h; from about 100/h to about 1,000/h; from about 250/h to about 1,000/h; or from about 500/h to about 1,000/h, depending upon, for example, the particular catalyst used and the temperature of the reactor and/or catalyst bed. In one aspect, the reactor and/or a dehydrogenation process can be operated at a temperature of from about 520° C. to about 650° C., for example, about 520, 530, 540, 550, 560, 570, 580, 590, 600, 610, 620, 630, 640, or 650° C. It should be noted that the space velocities and temperatures recited herein for hydrogenation and dehydrogenation reactions are intended to be exemplary and are not intended to be limiting. Accordingly, values lower than or greater than those recited herein are also intended to be included.

In another aspect, the inventive reactor design can exhibit a pressure drop of from about 0.05 bar to about 100 bar, for example, about 0.05, 0.1, 0.5, 1, 2, 3, 4, 5, 8, 10, 15, 20, 25, 30, 35, 40, 45, 50, 55, 60, 65, 70, 75, 80, 85, 90, 95, or 100 bar during operation. In other aspects, the inventive reactor design can exhibit a pressure drop of from about 5 bar to about 100 bar, of from about 10 bar to about 100 bar, of from about 40 bar to about 100 bar, of from about 0.05 bar to about 50 bar, or of from about 0.05 bar to about 10 bar, or from about 0.05 bar to about 5 bar, during operation.

Similarly, the inventive reactor design can be operated, for example, in a hydrogenation and/or dehydrogenation process, at a pressure of from about 1 psig to about 500 psig, for example, about 1, 5, 15, 25, 35, 45, 55, 75, 95, 115, 135, 155, 175, 195, 215, 235, 255, 275, 295, 315, 335, 355, 375, 395, 415, 435, 455, 475, or 500 psig. In other aspects, the inventive reactor and/or process can be operated at a pressure of from about 50 to about 500 psig, from about 100 to about 500 psig, from about 200 to about 500 psig, from about 1 to about 400 psig, from about 1 to about 100 psig, or from about 1 to about 10 psig. In yet another aspect, the reactor and/or process can be operated at other pressures above or below any values specifically recited herein, and the present invention is not intended to be limited to any particular pressure value or range.

In another aspect, the inventive reactor and/or process can utilize a catalyst having an average surface area of from about 15 m$^2$/g to about 650 m$^2$/g, for example, about 15, 20, 25, 30, 35, 40, 50, 75, 100, 125, 150, 175, 200, 225, 250, 275, 300, 325, 350, 375, 400, 425, 450, 475, 500, 525, 550, 575, 600, 625, or 650 m$^2$/g; or from about 20 m$^2$/g to about 650 m$^2$/g; from greater than about 20 m$^2$/g to about 650 m$^2$/g; from about 25 m$^2$/g to about 650 m$^2$/g; from about 30 m$^2$/g to about 650 m$^2$/g; from about 50 m$^2$/g to about 650 m$^2$/g; from about 100/g to about 650 m$^2$/g; or from about 25 m$^2$/g to about 500 m$^2$/g. Similarly, the catalyst can comprise a porous zeolite support having an average pore size of from about 1 Å to about 20 Å, for example, about 1, 2, 3, 4, 5, 6, 7, 8, 9, 10, 11, 12, 13, 14, 15, 16, 17, 18, 19, or 20 Å; from about 5 Å to about 20 Å; from about 10 Å to about 20 Å; from about 1 Å to about 15 Å; or from about 1 Å to about 10 Å. In other aspects, the catalyst can comprise a meso-porous support having an average pore size of from about 20 Å to about 500 Å, for example, about 20, 30, 40, 50, 75, 100, 125, 150, 175, 200, 225, 250, 275, 300, 325, 350, 375, 400, 425, 450, 475, or 500 Å. In other aspects, the catalyst can comprise a meso-porous support having an average pore size of from about 50 Å to about 500 Å, from about 100 Å to about 500 Å, from about 20 Å to about 300 Å, from about 20 Å to about 200 Å, or from about 20 Å to about 100 Å. In other aspects, other catalysts and/or supports having surface areas and/or pore sizes not recited herein can be used, and the present invention is not intended to be limited to any particular surface area and/or pore size of catalyst and/or catalyst support.

Figure 1:
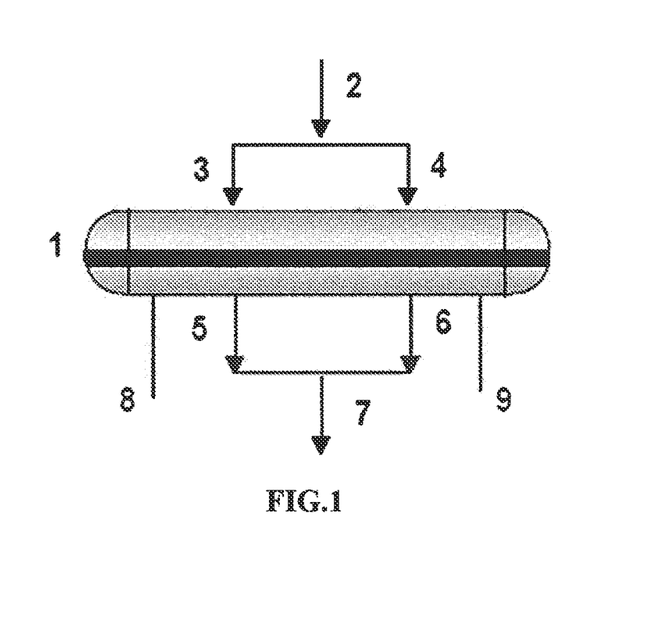
FIG. 1 illustrates a reactor design having two feed inlets and two outlets, in accordance with various aspects of the present disclosure.
Figure 2:
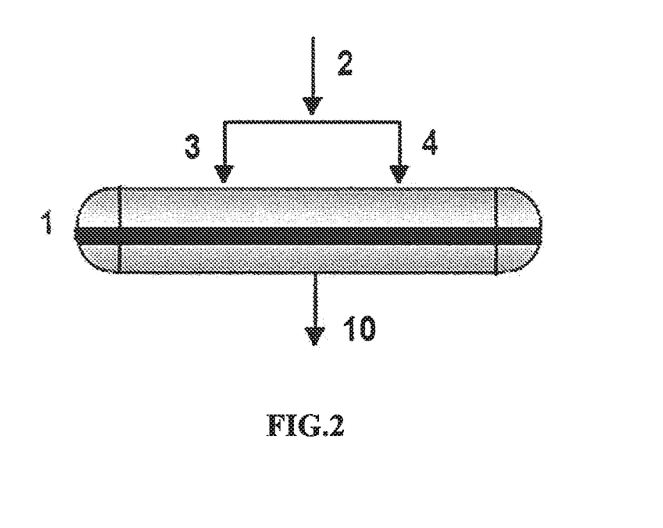
FIG. 2 illustrates a reactor design having two feed inlets and a single outlet, in accordance with various aspects of the present disclosure.

With reference to the Figures, FIG. 1 illustrates a reactor design having two feed inlets 3, 4, which equally, or approximately equally divide the feed from main inlet 2. Through the two feed inlets 3, 4, the feed material can enter the reactor 1. The reaction products, byproducts, and/or unreacted feed material can then leave the reactor from outlets 5, 6, which are subsequently combined downstream into a single flow 7. The flow from the combined outlet 7 can then be directed to other units, to a separate reactor of the same or differing design, or to a collection vessel. The use of a plurality of inlets, as illustrated in FIG. 1, can facilitate a semi-batch operation mode, which can be useful for catalysts requiring frequent regeneration. The reactor can optionally comprise a dip tray 8, 9, that can help in draining or recovering condensate and/or green oil. In another aspect, as illustrated in FIG. 2, the reactor can be configured to have a plurality of inlets 3, 4, and a single outlet 10.

Figure 3:
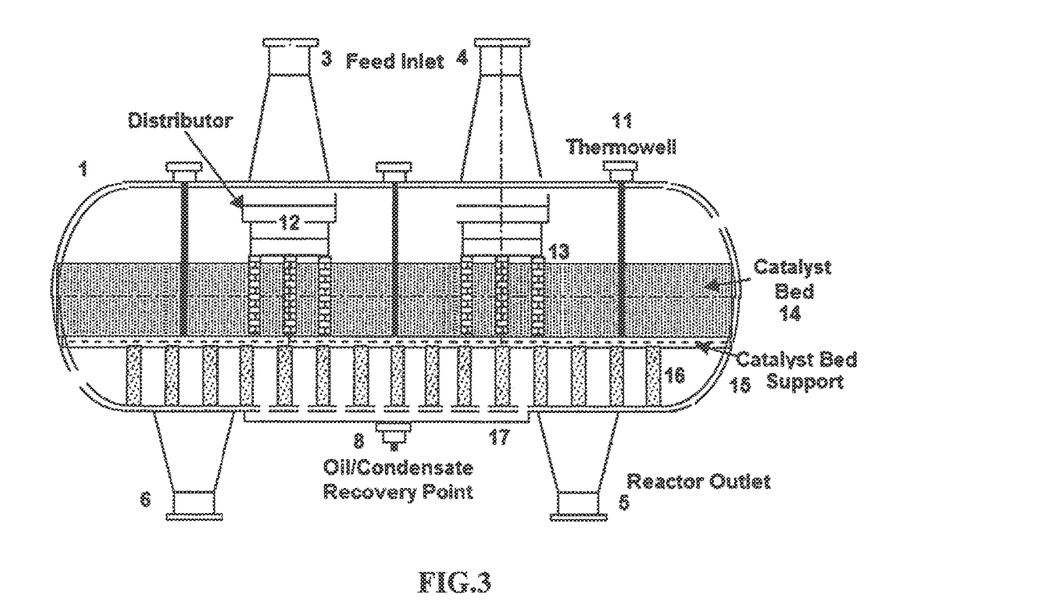
FIG. 3 illustrates a cross-section view of a reactor design having two feed inlets and two outlets, in accordance with various aspects of the present disclosure.

A cross-sectional illustration of a reactor comprising a plurality of inlets 3, 4, and a plurality of outlets 5, 6, is illustrated in FIG. 3. In FIG. 3, feed inlet nozzles 3, 4, convey feed material to distributors 12, 13, which uniformly distribute the feed material over the catalyst bed 14. The catalyst bed is supported by supports 15, 16. A thermowell 11 can be used to monitor the temperature of the catalyst bed and effectively control any hotspot and/or runaway conditions that may occur. In addition, condensate and/or green oil can be collected in dip tray 17 and collected from separate collection outlet 8, without affecting the operation of the reactor.

Figure 4:
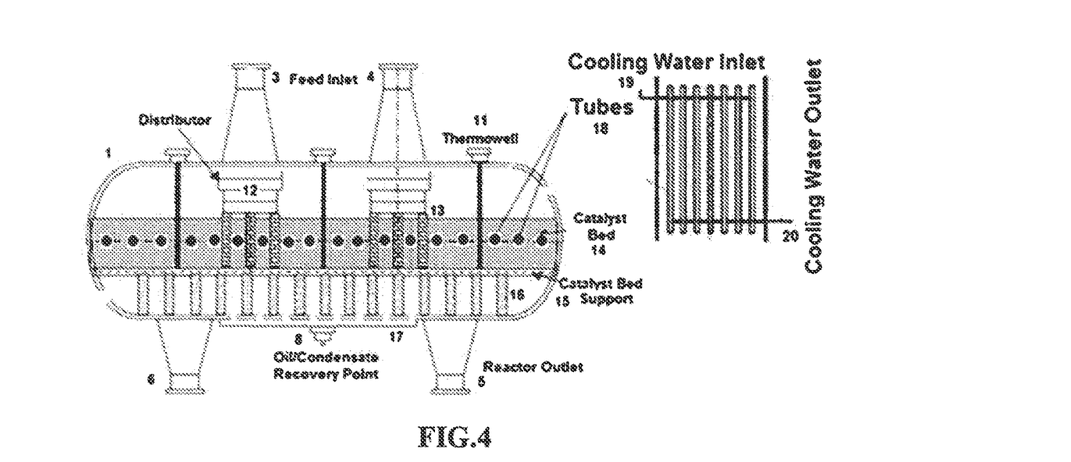
FIG. 4 illustrates a cross-section view of a reactor design having two feed inlets and two outlets, together with integrated cooling tubes, in accordance with various aspects of the present disclosure.

The reactor 1 can optionally comprise integrated tubes 18 for adjusting the temperature of the catalyst bed. In one aspect, such tubes can be used to convey cooling water through the catalyst bed 14. Such tubes can be connected to an inlet 19 for cooling water and an outlet 20 for the used cooling water, as illustrated in FIG. 4.

Figure 5:
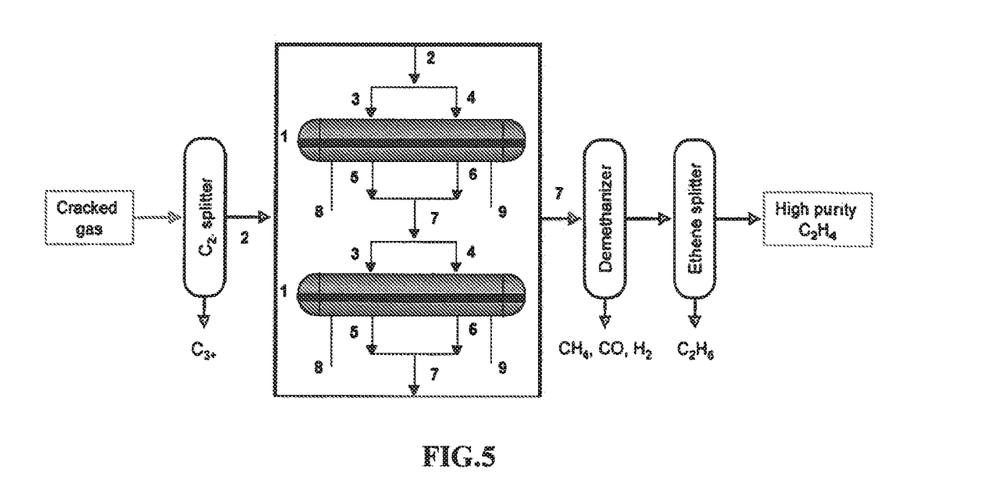
FIG. 5 illustrates a front-end hydrogenation process, in accordance with various aspects of the present disclosure.
Figure 6:
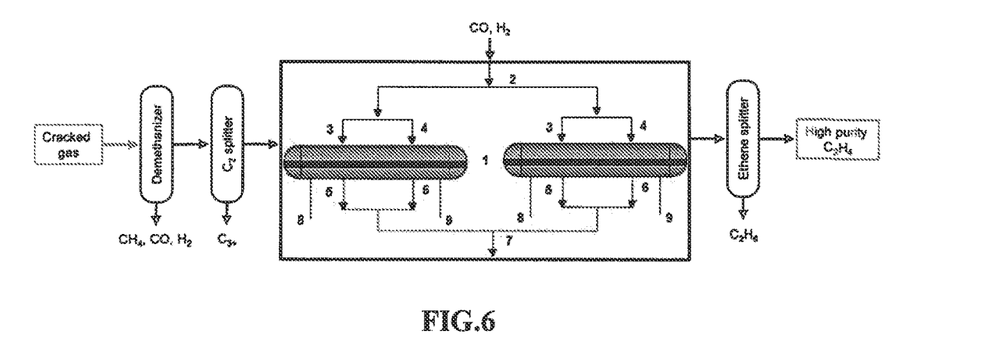
FIG. 6 illustrates a back-end hydrogenation process, in accordance with various aspects of the present disclosure.

FIG. 5 illustrates an exemplary front-end hydrogenation process wherein two reactors are employed in a series configuration downstream of a $C_2$ splitter and upstream of a demethanizer. FIG. 6 illustrates an exemplary back-end hydrogenation process wherein two reactors are employed in a parallel configuration downstream of a demethanizer and $C_2$ splitter.

In another aspect, the particular type and/or concentration of a given impurity, such as, for example, $CO$, $CO_2$, $O_2$, and/or other impurities or combinations thereof can vary depending upon the placement of a given reactor within a process, for example, as a front-end or back-end technology. In yet another aspect, the selection of a given catalyst can similarly vary, and one of skill in the art, in possession of this disclosure, could readily select an appropriate reactor configuration and/or catalyst for a desired reaction.

It should be appreciated that the methods and reactor designs of the present invention can be described in any of a number of exemplary and non-limiting aspects, such as those recited below.

Aspect 1: A reactor suitable for use in a hydrogenation and/or a dehydrogenation process, the reactor comprising: a catalyst bed, a plurality of inlets for conveying a feed material to the catalyst bed, and one or more outlets, wherein the catalyst bed comprises a catalyst having a surface area of from about 15 $m^2/g$ to about 650 $m^2/g$, and wherein the reactor can provide at least one of a space velocity of from about 500/h to about 50,000/h for hydrogenation reactions or a space velocity of from about 1/h to about 1,000/h for dehydrogenation reactions.

Aspect 2: The reactor of Aspect 1, further comprising one or more distributors for distributing the feed material uniformly or substantially uniformly across the catalyst bed.

Aspect 3: The reactor of Aspect 1 or 2, wherein the catalyst bed is a fixed bed comprising a selective hydrogenation and/or dehydrogenation catalyst.

Aspect 4: The reactor of any of Aspects 1-3, wherein the catalyst bed is positioned in contact with one or more catalyst bed supports.

Aspect 5: The reactor of any of Aspects 1-4, being a hydrogenation reactor comprising a plurality of inlets for an olefin feed, an oxygenate feed, or a combination thereof.

Aspect 6: The reactor of any of Aspects 1-5, further comprising a drip trap for recovering a condensate and/or a green oil.

Aspect 7: The reactor of any of Aspects 1-6, further comprising one or more thermowells disposed between an exterior surface of the reactor and the catalyst bed.

Aspect 8: The reactor of any of Aspects 1-7, further comprising a means for adjusting the temperature of the catalyst bed.

Aspect 9: The reactor of any of Aspects 1-8, wherein the catalyst bed comprises a heating and/or a cooling element.

Aspect 10: The reactor of any of Aspects 1-9, wherein the catalyst bed comprises a tube for cooling the catalyst bed.

Aspect 11: The reactor of any of Aspects 1-10, wherein the catalyst has a surface area of from about 30 $m^2/g$ to about 650 $m^2/g$.

Aspect 12: The reactor of any of Aspects 1-11, having a space velocity of at least about 25,000/h.

Aspect 13: The reactor of any of Aspects 1-12, having a high space velocity, a low pressure drop, a uniform distribution of feed material across the catalyst bed, or a combination thereof, as compared to a conventional hydrogenation and/or dehydrogenation reactor.

Aspect 14: A reactor system comprising a plurality of the reactors of any of Aspects 1-12, arranged in a series configuration.

Aspect 15: A reactor system comprising a plurality of the reactors of any of Aspects 1-12, arranged in a parallel configuration.

Aspect 16: A method for a dehydrogenation process, the method comprising introducing a feed material to the reactor of any of Aspects 1-12 through the plurality of inlets, such that the feed material uniformly or substantially uniformly contacts the catalyst bed to produce a reaction product.

Aspect 17: The method of Aspect 16, wherein the feed material comprises one or more saturated hydrocarbons, and wherein at least a portion of the one or more saturated hydrocarbons is converted into an olefin.

Aspect 18: The method of Aspect 16, wherein the reaction product comprises a purified alkene.

Aspect 19: A method for a hydrogenation process, the method comprising introducing a feed material to the reactor of any of Aspects 1-12 through the plurality of inlets, such that the feed material uniformly or substantially uniformly contacts the catalyst bed to produce a reaction product.

Aspect 20: The method of Aspect 19, wherein the feed material comprises acetylene, and wherein the reaction produce comprises an alkene.

Aspect 21: The method of Aspect 16, wherein the reactor provides a space velocity of from about 1/h to about 1,000/h.

Aspect 22: The method of Aspect 19, wherein the reactor provides a space velocity of from about 500/h to about 50,000/h.

Aspect 23: The method of Aspect 16 or 19, wherein the reactor exhibits a pressure drop of from about 0.05 to about 100 bar.

Aspect 24: The method of Aspect 16 or 19, wherein the reactor provides improved control over runaway reactions, as compared to a conventional reactor.

Aspect 25: The method of Aspects 16 or 19, wherein a plurality of reactors are connected in a series configuration to provide a front-end acetylene removal system.

Aspect 26: The method of Aspects 16 or 19, wherein a plurality of reactors are connected in a parallel configuration to provide a back-end acetylene removal system.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A reactor suitable for use in a hydrogenation process, the reactor comprising:
   a. a catalyst bed comprising a tube for cooling the catalyst bed;
   b. a plurality of inlets for conveying a feed material to the catalyst bed; and
   c. one or more outlets,
   wherein the catalyst bed comprises a catalyst having a surface area of from about 15 $m^2/g$ to about 650 $m^2/g$, and wherein the reactor can provide a space velocity of from about 500/h to about 50,000/h for hydrogenation reactions.

2. The reactor of claim 1, further comprising one or more distributors for distributing the feed material uniformly or substantially uniformly across the catalyst bed.

3. The reactor of claim 1, wherein the catalyst bed is a fixed bed comprising a selective hydrogenation catalyst.

4. The reactor of claim 1, wherein the catalyst bed is positioned in contact with one or more catalyst bed supports.

5. The reactor of claim 1, being a hydrogenation reactor comprising a plurality of inlets for an olefin feed, an oxygenate feed, or a combination thereof.

6. The reactor of claim 1, further comprising a drip trap for recovering a condensate and/or a green oil.

7. The reactor of claim 1, further comprising one or more thermowells disposed between an exterior surface of the reactor and the catalyst bed.

8. The reactor of claim 1, wherein the catalyst has a surface area of from about 30 $m^2/g$ to about 650 $m^2/g$.

9. The reactor of claim 1, having a space velocity of at least about 25,000/h.

10. The reactor of claim 1, having a high space velocity, a pressure drop from about 0.05 bar to about 100 bar, a uniform distribution of feed material across the catalyst bed, or a combination thereof.

11. A reactor system comprising a plurality of the reactor of claim 1, arranged in a series configuration.

12. A reactor system comprising a plurality of the reactor of claim 1, arranged in a parallel configuration.

13. A method for a hydrogenation process, the method comprising introducing a feed material to the reactor of claim 1 through the plurality of inlets, such that the feed material uniformly or substantially uniformly contacts the catalyst bed to produce a hydrogenation reaction product.

14. The method of claim 13, wherein the feed material comprises acetylene, and wherein the reaction product comprises an alkene.

15. The method of claim 13, wherein the reactor exhibits a pressure drop of from about 0.05 to about 100 bar.

16. The method of claim 13, wherein the reactor provides improved control over runaway reactions, as compared to a conventional reactor.

17. The method of claim 13, wherein a plurality of the reactor are connected in a series configuration to provide a front-end acetylene removal system.

18. The method of claim 13, wherein a plurality of the reactor are connected in a parallel configuration to provide a back-end acetylene removal system.

* * * * *